United States Patent
Livingston (10) Patent No.: US 11,607,204 B2
(45) Date of Patent: Mar. 21, 2023

(54) PACKAGING AND DEVICES TO ACCESS SCREW-TOP CONTAINERS IN AUTOMATED SYSTEMS

(71) Applicant: BECTON DICKINSON AND COMPANY, Franklin Lakes, NJ (US)

(72) Inventor: Dwight Livingston, Fallston, MD (US)

(73) Assignee: BECTON DICKINSON AND COMPANY, Franklin Lakes, NJ (US)

(*) Notice: Subject to any disclaimer, the term of this patent is extended or adjusted under 35 U.S.C. 154(b) by 769 days.

(21) Appl. No.: 16/078,111

(22) PCT Filed: Mar. 1, 2017

(86) PCT No.: PCT/US2017/020208
§ 371 (c)(1),
(2) Date: Aug. 21, 2018

(87) PCT Pub. No.: WO2017/151774
PCT Pub. Date: Sep. 8, 2017

(65) Prior Publication Data
US 2019/0038264 A1    Feb. 7, 2019

Related U.S. Application Data

(60) Provisional application No. 62/302,455, filed on Mar. 2, 2016.

(51) Int. Cl.
*A61B 10/00* (2006.01)
*B65D 71/50* (2006.01)
(Continued)

(52) U.S. Cl.
CPC ...... *A61B 10/0096* (2013.01); *B01L 3/50825* (2013.01); *B01L 3/50855* (2013.01);
(Continued)

(58) Field of Classification Search
CPC ............... A61B 10/0096; B01L 3/5082; B01L 3/50825; B01L 3/5085; B01L 3/50853;
(Continued)

(56) References Cited

U.S. PATENT DOCUMENTS 3,690,495 A * 9/1972 Turner ................ B65D 50/041
                                                215/220
5,501,322 A * 3/1996 Drebushenko ......... B65D 71/50
                                                206/147
(Continued)

FOREIGN PATENT DOCUMENTS

| EP | 1803499 A1 | 7/2007 |
| WO | 9400238 A1 | 1/1994 |
| WO | 2015056229 A1 | 4/2015 |

OTHER PUBLICATIONS

International Search Report issued in corresponding PCT application No. PCT/US2017/020208 dated May 26, 2017.
(Continued)

*Primary Examiner* — Benjamin R Whatley
*Assistant Examiner* — Austin Q Le
(74) *Attorney, Agent, or Firm* — Botos Churchill IP Law LLP (57) ABSTRACT

The present invention relates to a system for access and retrieval of screw-top containers. In one embodiment, the system includes a tray with a plurality of apertures, the tray adapted to receive containers having a cap and a body such that each cap of each container pressed into the tray rests above a respective aperture in the tray and each body is suspended below the tray. The system also includes a rotary tool having a cavity extending from an opening at one end, the cavity defined by an interior surface that includes engagement features. The engagement features on the interior surface of the rotary tool are adapted to engage onto at least a portion of the body of the container surface defined (Continued)

by complementary engagement features when the rotary tool is inserted over the body of the container from below the tray.

6 Claims, 4 Drawing Sheets

(51) Int. Cl.
*B65D 41/04* (2006.01)
*B65D 71/00* (2006.01)
*B01L 3/00* (2006.01)
*B01L 9/06* (2006.01)
*G01N 35/04* (2006.01)

(52) U.S. Cl.
CPC ............ *B01L 9/06* (2013.01); *B65D 41/04* (2013.01); *B65D 71/00* (2013.01); *B65D 71/50* (2013.01); *B01L 2200/025* (2013.01); *B01L 2300/0829* (2013.01); *G01N 2035/0405* (2013.01)

(58) Field of Classification Search
CPC .. B01L 3/50855; B01L 9/06; B01L 2200/025; B01L 2200/0829; B01L 2300/0829; B01L 2300/0832; B65D 41/04; B65D 41/0407; B65D 41/0414; B65D 41/0428; B65D 41/0442; B65D 71/00; B65D 71/50; G01N 2045/0405
See application file for complete search history.

(56) References Cited

U.S. PATENT DOCUMENTS

| | | | |
|---|---|---|---|
| 5,837,198 A | 11/1998 | Itani | |
| 7,316,805 B1 | 1/2008 | Viola et al. | |
| 7,340,324 B2 | 3/2008 | Heath et al. | |
| 7,985,375 B2 | 7/2011 | Edens et al. | |
| 8,142,740 B2 | 3/2012 | Self et al. | |
| 8,357,538 B2 | 1/2013 | Self et al. | |
| 8,703,492 B2 | 4/2014 | Self et al. | |
| 9,199,755 B1* | 12/2015 | Cohen | A47B 81/007 |
| 2005/0165287 A1 | 7/2005 | Wescott, III | |
| 2005/0277848 A1* | 12/2005 | Graf | A61B 10/0096 |
| | | | 600/575 |
| 2007/0104617 A1* | 5/2007 | Coulling | B01L 3/50825 |
| | | | 422/400 |
| 2008/0035642 A1* | 2/2008 | Esser | B01L 3/50855 |
| | | | 220/315 |
| 2009/0272237 A1* | 11/2009 | Pirseyedi | B25B 13/44 |
| | | | 81/125 |
| 2014/0361022 A1 | 12/2014 | Finneran | |

OTHER PUBLICATIONS

Extended European Search Report issued in corresponding EP application No. 17760720.7 dated Jul. 31, 2019.
Office Action issued in corresponding Chinese application No. 201780012889.7 dated Jan. 22, 2020.
Search Report issued in corresponding Chinese application No. 201780012889.7 dated Jan. 22, 2020.
Office Action issued in corresponding European application No. 17760720.7 dated Jun. 29, 2020.
Office Action issued in corresponding Korean Patent Application No. 10-2018-7026566 dated May 14, 2021, 15 pp.
Notification of Reasons for Refusal issued in Japanese application No. 2018-546538 dated Mar. 2, 2021.
Indian Office Action for Application No. 201817032499 dated Jun. 21, 2021 (5 pages).
Office Action issued in corresponding Australian Patent Application No. 2017227704 dated Dec. 17, 2021, 3 pp.

* cited by examiner

PACKAGING AND DEVICES TO ACCESS SCREW-TOP CONTAINERS IN AUTOMATED SYSTEMS

CROSS-REFERENCE TO RELATED APPLICATIONS

This application claims the benefit of the filing date of U.S. Provisional Patent Application No. 62/302,455, filed Mar. 2, 2016, the disclosure of which is hereby incorporated by reference herein.

BACKGROUND OF THE INVENTION

The ability to remove a cap from a container when the container is positioned on a tray is an important part of the testing and analysis of the contents of such containers (e.g., reagents, samples, etc.). Often, a capped container is stored at a location in an instrument and then transported to another location for further processing that requires access to the contents (e.g., aspiration of contents from the container or dispense of substances into the container), and then returned to the original instrument for storage. The substances (e.g., reagents, samples, etc.) dispensed into the container or aspirated from the container are typically liquid and a pipette (either manual or automated) is used to dispense or aspirate such substances. During these steps, the container cap must be removed to access the interior of the container to dispense the substances into or aspirate the contents from the container. However, systems and methods available to perform cap removal typically require that a cap be removed from a container from above. Once the cap is removed, the container can be separately removed from the tray for transport to another location. This process must be repeated in reverse once pipetting or another applicable procedure is completed and the container is ready to be placed back into storage.

For example, a plurality of containers with caps are positioned in wells within a rack or tray. To open a desired container and transport same, either manually or using an automated approach, the desired container must first be held in place. Then, the cap of the container must be engaged. If the cap is attached via a screw thread, it must be spun to be removed. Once removed, the cap must be placed at another location for temporary storage. After these steps are completed, the opened container itself is picked up for transport to another location. When the desired procedure, such as pipetting, is completed, the process must be repeated if the container is to be placed back onto the rack or tray. If not, the process must still be repeated for any further containers to be opened and transported. The necessity of these steps makes the decapping process expensive, cumbersome and increases the likelihood of error due to the complexity of the process. Removal and reattachment of a cap relative to a container is described in U.S. Pat. Nos. 7,985,375, 7,340,324 and 7,316,805, hereby incorporated by reference herein. Removal of containers from a tray from above using an automated system is described in U.S. Pat. No. 8,142,740, hereby incorporated by reference herein.

In some cases, racks have been developed that provide suspended storage for containers (e.g., tubes). In one example of such a system, described in U.S. Pat. Nos. 8,703,492 and 8,357,538, hereby incorporated by reference herein, the rack includes recesses that allow for engagement to the rack from above. In particular, the frame, or rack, includes recesses at enlarged ends that create spaces between frames when they are packed closely together. This allows each frame to be grasped from above, because the recesses are accessible from a top surface of the frame, and tubes suspended under the frame prevent access to the frame from below.

Accordingly, existing systems and methods do not simplify the separation of a container body from a respective cap when it is desired to transport the container body to another location. Accordingly alternative methods and devices for separating caps from containers continue to be sought.

BRIEF SUMMARY OF THE INVENTION

The present invention relates to technology for capping and decapping containers stored in large quantities in trays. In processing, the caps must be removed from the containers in order to remove substances from the container or dispense contents into the container. After such removal or dispense, the caps are replaced. Such containers are used for many different purposes. In one embodiment, the container is used to assay a sample (e.g., a biological or environmental sample). In the context of the assay, samples and reagents used to prepare and process the assay for the sample are dispensed into and removed from the container. There are a variety of assays that deploy such capped containers. One exemplary assay is molecular testing of the sample. In particular, the invention addresses reduction in the number of structural components necessary and the effort required to decap and transport containers. It is understood from the general description herein that the capped containers can either hold contents or be empty. Once the cap is removed, as described herein, the interior of the container is accessible and substances such as samples, reagents, etc. can be dispensed into or removed from the containers as required.

In a first aspect, a system is provided to access and retrieve screw-top containers. One embodiment of the system includes a tray and a rotary tool. The tray includes a plurality of apertures and each aperture is adapted to receive a container that has a cap and a body. The tray receives containers pressed into a respective tray aperture and when in place, each container cap rests above a respective aperture in the tray and each container body is suspended from the aperture. The rotary tool has a cavity that extends from an opening at one end where the cavity is defined by an interior surface. The interior surface of the cavity includes protrusions. The protrusions on the interior surface of the rotary tool are adapted to engage onto at least a portion of the body of the container surface defined by protrusions. Engagement occurs when the rotary tool is inserted over the body of the container from below the tray. When so engaged, rotation of the rotary tool will cause the body of the container to rotate.

In another embodiment, a second end of the rotary tool opposite the end with the opening includes a surface adapted for use as a handle. In a further embodiment, the protrusions on the interior surface of the rotary tool and on the surface of the container body are longitudinally oriented splines.

In yet another embodiment, the tray and container caps are monolithic. In these embodiments, the container is received by the cap that is integral with the tray. In other embodiments, the shape of the tray proximal to each aperture is adapted to guide the body of the container into the cap above a surface of the tray as the container is pressed into the tray from below.

In other embodiments, an outer circumferential surface of the cap includes knurling that provides resistance to rotation when positioned in the tray. Correspondingly, tubular extensions extend from the tray that are sized to interact with respective caps placed through apertures in the tray. The tubular extensions include interior surfaces that have knurled surfaces.

In any of the above embodiments, the system can also include a container holder. The container holder includes an aperture defined by an interior surface on a circumference of the aperture. The interior surface of the aperture includes a screw thread such that the body of the container can be screwed into the aperture from below.

Another embodiment of the system includes a tray, a socket member and a socket rotary tool. The tray includes a plurality of apertures. Each aperture is sized so that a container body, but not its cap, can pass through the aperture. The tray is adapted to receive containers having a cap and body. When each container body is fully pressed into the tray, the cap rests above the aperture in the tray and respective container bodies are suspended below the tray.

The socket member has a length between a first end and a second end. At the first end is a polygonal shaped cavity that extends inward in a longitudinal direction toward the second end. At the second end is a circular cavity that extends inward in a longitudinal direction toward the first end. On an inner surface defining a circumference of the circular cavity proximal to the second end are protrusions. The protrusions are adapted to engage corresponding protrusions on containers suspended from the tray. The length of the cavity extending inward from the first end and the cavity extending inward from the second end, when combined, is less than the entire length of the socket member so that only one cavity is present at any point along the length of the socket member.

The socket rotary tool includes a handle portion and an engagement portion. The engagement portion includes a polygonal cross-sectional shape adapted to fit within the polygonal shaped cavity in the socket member.

In other embodiments, the socket member is cylindrical in shape and includes two recessed portions along its length. Each recessed portion is recessed from an outer surface of the socket member and includes anti-rotation features on its surface. In a variant, the system also includes a socket holder. The socket holder includes an upper and lower flange that both extend from a central portion in a transverse direction. Each flange includes an edge with recesses adapted to secure the recessed portions of the socket member within.

In another embodiment, a shape of a surface on the tray proximal to each aperture is adapted to guide the body of the container into the cap above the surface of the tray. The cap can be monolithically integrated with the tray. In other embodiments, an outer circumferential surface of the cap includes knurling that provides resistance to rotation when positioned in the tray. In the inserted position, the knurling on the caps interfaces with corresponding knurling on an interior surface of tubular extensions extending from a tray surface and sized to surround caps at each aperture of the tray.

In yet another embodiment, the protrusions on the interior surface of the socket member and on the surface of the container body are longitudinally oriented splines.

In another aspect, the present invention relates to a method of removing a body of a screw-top container from a tray. In one embodiment, the method includes the step of transporting a rotary tool to a location below the tray. The tray includes a plurality of apertures on its surface and houses one or more containers. The containers are housed so that respective bodies of the containers are suspended from apertures on the tray. In this position, a cap of each container rests above the aperture.

The transporting step is followed by positioning the rotary tool such that an opening at one end of the tool is facing upward toward one of the containers. This is followed by sliding the rotary tool over the container suspended below the tray so that protrusions on an inner surface of the rotary tool align with corresponding protrusions on the surface of the container. This forms an interlocking connection between the tool and the container.

Removal of the container is completed by rotating the rotary tool in a counterclockwise direction. This detaches the body of the container from the corresponding cap as the interlocking connection between the tool and the body causes the rotary tool to rotate in unison with the body of the container.

In another embodiment, an additional step is taken of placing the one or more containers into the tray from above the tray prior to positioning the rotary tool below the tray. In yet another embodiment, transporting the rotary tool containing the body of the container involves transporting to a container holder adapted to secure the body of a container to an aperture in the container holder. The body of the container can also be placed into the container holder from below using the rotary tool by rotating the rotary tool in the clockwise direction. This connects the body of the container to the aperture in the container holder defined by an inner surface having a screw thread because the screw thread of the body interconnects with the screw thread of the container holder aperture.

In yet another embodiment, a system to access and retrieve screw-top containers includes a tray including a plurality of apertures. The tray is adapted to receive containers having a cap and a body such that each cap of each container pressed into the tray rests above a respective aperture in the tray and each body is suspended below the tray. The system also includes a rotary tool having a cavity extending from an opening at one end. The cavity is defined by an interior surface that includes engagement features. The engagement features on the interior surface of the rotary tool are adapted to engage onto at least a portion of the body of the container surface defined by complementary engagement features when the rotary tool is inserted over the body of the container from below the tray. In a variant, the first or second engagement features are protrusions.

In another embodiment, a system to access and retrieve screw-top containers includes a tray including a plurality of apertures, where the apertures are sized to accommodate a cross-sectional area of a container. The tray is adapted to receive containers having a cap and body such that each cap of each container placed into the tray rests above a respective aperture in the tray and each body is suspended below the tray. The system also includes a socket member having a length between a first end and a second end, a first cavity in the socket member having a first cross-section extending longitudinally from the first end toward the second end and a second cavity in the socket member having a second cross-section extending longitudinally from the second end toward the first end, an inner surface defining a circumference of the second cavity wherein engagement features are located on the inner surface proximate the second end, the engagement features adapted to grip onto corresponding engagement features on containers suspended from the tray. The first and second cavity abut one another to define a single passage through the socket member or are separated from one another. The system also includes a socket rotary tool having a handle portion and an engagement portion, the engagement portion having a cross-sectional shape adapted to fit within the first cavity in the socket member.

Another embodiment involves a method of removing a body of a screw-top container from a tray. The method includes the step of transporting a rotary tool to a location below the tray. The tray includes a plurality of apertures on its surface and houses one or more containers. The containers are housed so that respective bodies of the containers are suspended from apertures on the tray. In this position, a cap of each container rests above the aperture. The transporting step is followed by positioning the rotary tool such that an opening at one end of the tool is facing upward toward one of the containers. This is followed by sliding the rotary tool over the container suspended below the tray so that engagement features on an inner surface of the rotary tool align with corresponding engagement features on the surface of the container. This forms an interlocking connection between the tool and the container. Removal of the container is completed by rotating the rotary tool in a counterclockwise direction. This detaches the body of the container from the corresponding cap as the interlocking connection between the tool and the body causes the rotary tool to rotate in unison with the body of the container.

DETAILED DESCRIPTION

The systems and methods described herein relate to trays and devices such as rotary tools that can be used together to remove bodies of containers from their respective caps so that the caps remain in the tray once the body is removed.

As used herein, "upward" means a side of a tray exposed to top surfaces of container caps.

As used herein, "sample" means a quantity of material from a biological, environmental, medical, or patient source in which detection or measurement of target cells, particles, beads, and/or analytes is sought. The term "sample" encompasses biological samples, e.g., a quantity of blood, a microbiological culture, or the like; environmental samples, e.g., a soil or water sample; medical samples or specimens, e.g., a quantity of blood or tissue; or the like. Preferably, a sample is a human blood sample. The terms "sample" and "specimen" are used interchangeably.

As used herein, "container" means any suitable vessel for receiving samples or specimens, as well as reagents for testing or preserving such samples or specimens. Such samples, specimens, and reagents can be in liquid or dry form. Containers or vessels can also be referred to as tubes, cuvettes, test wells, etc. The present invention is not limited to any type of container or any type of contents. In fact, in certain embodiments of the apparatus described herein the container used in conjunction with the apparatus can be empty.

Figure 1:
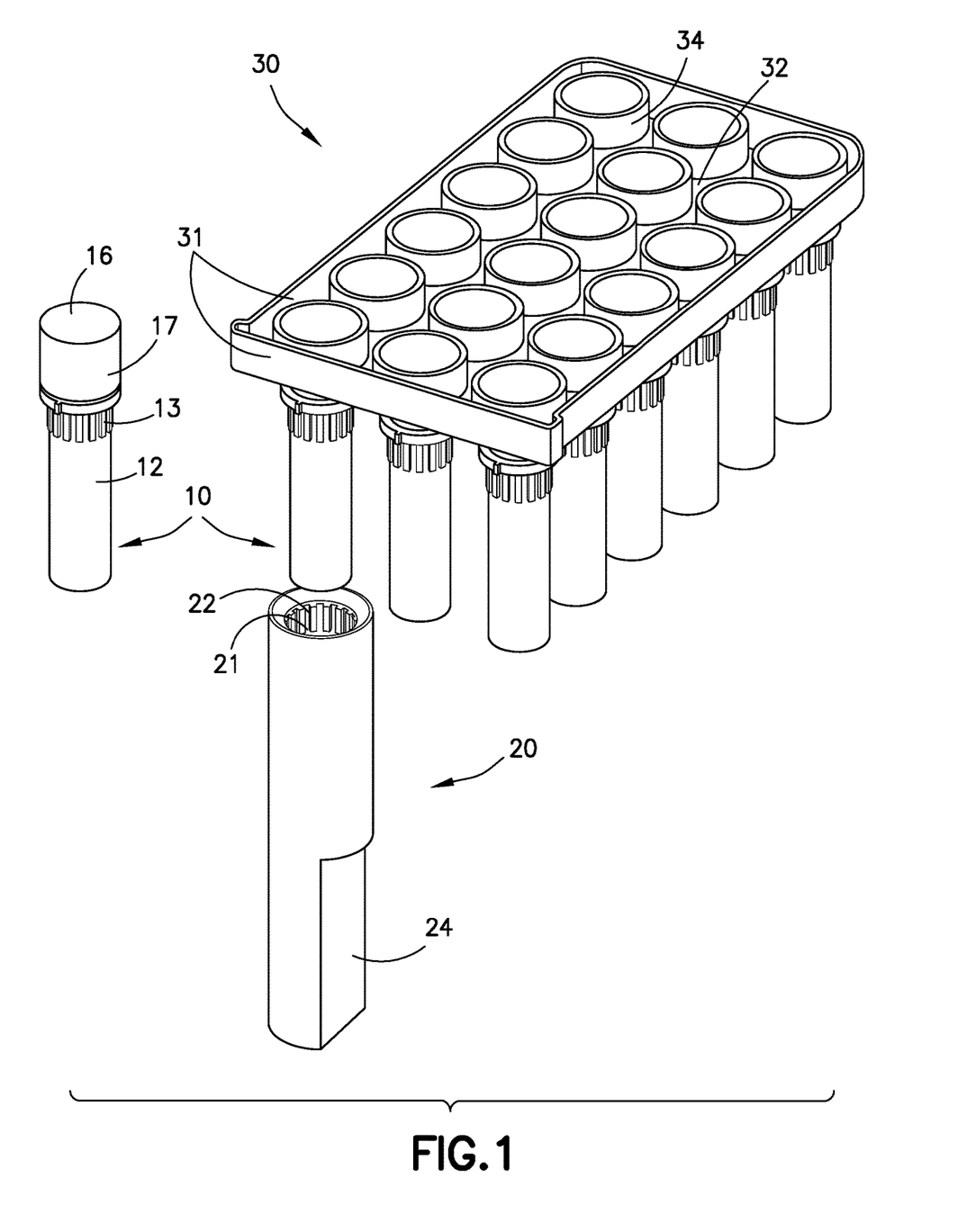
FIG. 1 illustrates a first embodiment including a tray holding a plurality of tubes, and a rotary tool and a tube is also shown as it appears outside of the tray.

In one aspect the present invention relates to a system adapted to remove a body of a container from a respective cap suspended by a tray and transport the container for pipetting or another use at different location. One embodiment of the first aspect is illustrated in FIG. 1. At a minimum, the system includes a rotary tool 20 and a tray 30 for storing a plurality of tubes 10.

Tubes 10 as shown in FIG. 1 include a body 12 and a cap 16. The cap of each tube is attached to the body via a screw thread 14. That is, each of an interior surface of the cap (not shown) and a corresponding exterior surface of the body includes a screw thread. A surface on the body of each tube further includes splines 13 oriented in a longitudinal direction. In a variant, the surface can include another feature in place of splines that provides an anti-rotation function when interlocked with a container having the same feature. One example of a tube is a reagent tube by Axygen.

Rotary tool 20 is cylindrical in shape and is sized to accommodate the size of tubes to be retrieved. For example, a length of the rotary tool can be adapted to any anticipated use with particular instrumentation or tube/container sizes. The rotary tool includes an opening at one end so that a portion of the length has a ring-shaped cross section with a substantially constant thickness. The thickness of the rotary tool is limited to allow it to fit between tubes in an array of tubes in a tray, as applicable. Further, on an interior surface 21 defining the outer bounds of a cavity extending from the opening of tool 20 are longitudinally oriented splines 22 designed to engage with capped tubes 10 suspended in tray 30. These are shown in FIG. 1 near the opening of tool 20 but can be placed further into the cavity of the tool as desired depending on the features of a tube sought to be retrieved. In a variant, the splines can be protrusions or other features known in the art that interlock with a tube having the same feature. In other variants, the splines can be located on a bottom surface of tube 10 and a bottom surface within the cavity of tool 20. When these surfaces make contact, the engagement ensures that each element moves in unison as the rotary tool is activated.

Splines 22 couple with matching splines 13 on the surface of body 12 of each tube 10. When tool 20 is placed over tube 10 and the splines are longitudinally aligned, the shape of the respective splined surfaces produce an interlocking feature restricting rotational movement of the body of the tube relative to the tool. Thus, once the respective components are interlocked or otherwise engaged, any rotation of the tool produces a corresponding rotation of the body of the tube.

In FIG. 1, tray 30 holds a plurality of tubes 10 in suspension. The tray is substantially rectangular in shape and includes upward facing flanges 31 around a perimeter. A top surface 32 includes apertures (not shown) for the placement of tubes therethrough. Typically, and as shown, these apertures are positioned in an array to provide for uniform spacing and a rectilinear arrangement of stored tubes. Surrounding the location of each aperture is a tubular extension 34 extending upward from top surface 32 of the tray. Tubular extension 34 has a constant thickness around its circumference sufficient to ensure structural integrity while tubes are stored, but is thin enough that the top surface of the tray is exposed and no tubular extensions are in contact with one another. An inner diameter of the tubular extension is large enough for body 12 of tube 10 to pass therethrough and for cap 16 of the tube to fit within. Tubular extension 34, and also the tray, are made of a deformable material such as molded plastic that allows tubular extension 34 to stretch upon placement of the tube into the tray. The inner diameter of the tubular extension is larger than a diameter of the corresponding aperture in the tray to ensure there is sufficient structure to support a cap while a tube is stored in the tray. In one variant, the tray can include lead-in features around the apertures in the tray that guide body 12 of the tube into the apertures of the tray as they are returned into the tray for storage after use.

Each tube 10 is suspended in tray 30 so that the cap rests on top surface 32 of the tray within tube extension 34 and body 12 of the tube secured to cap 16 is suspended and exposed underneath a bottom surface of the tray (not shown). Tubes 10 are supported by and suspended from the tray so that a length of each tube 10 is perpendicular to top surface 32 of the tray. As described above, each tube 10 includes splines 13 for engagement with rotary tool 20. When the capped tube is stored on the tray so that its cap rests on the top surface 32 of the tray, the splines of each tube 10 are accessible from underneath tray 30 as there is no obstruction of the tubes from directly below the tray. Therefore, the rotary tool can be positioned directly under the tube should retrieval of the tube body be desired.

Figure 2:
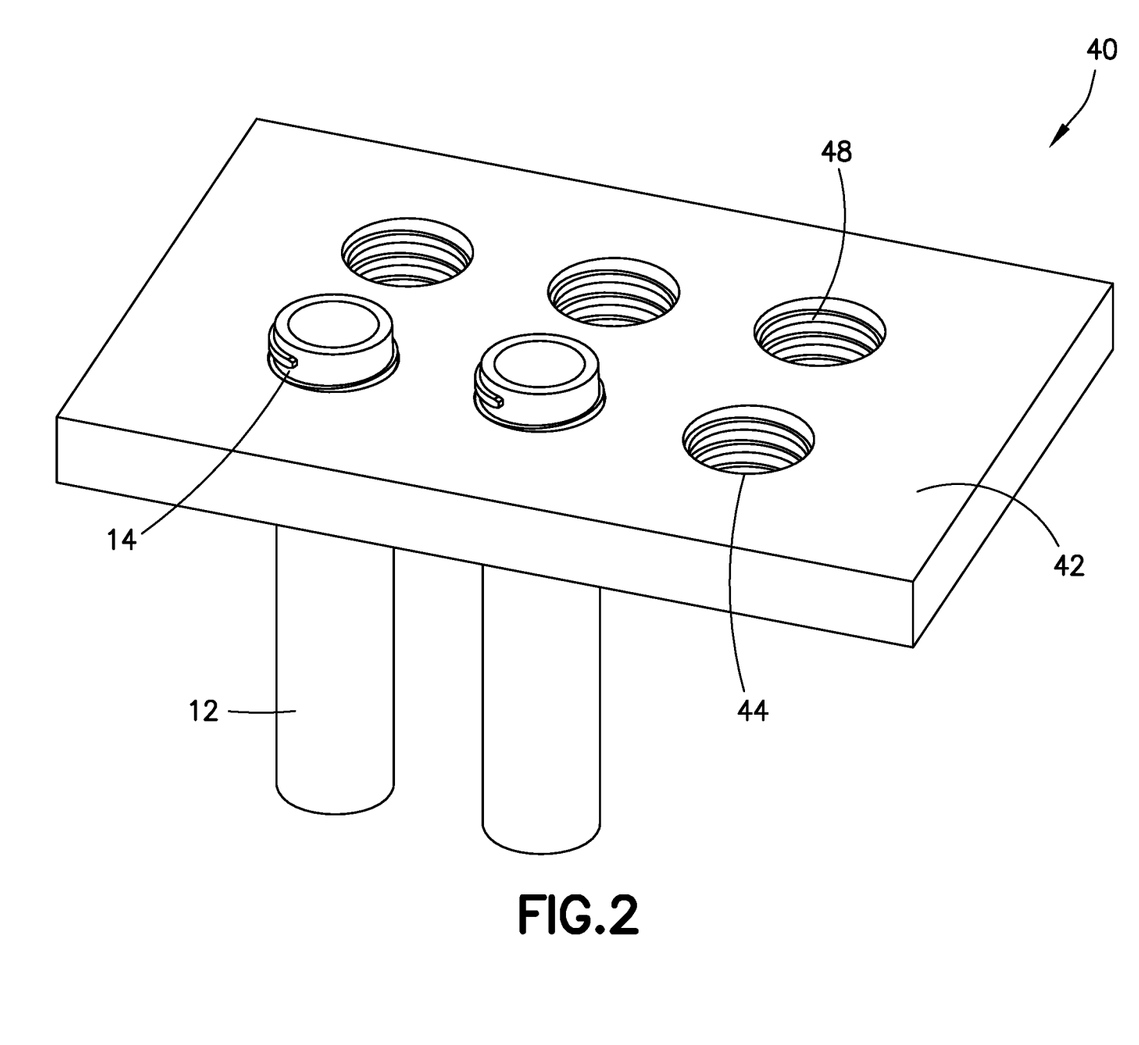
FIG. 2 illustrates a container holder for placement of the tube of the first embodiment illustrated in FIG. 1.

In a variant, the system also includes a container holder 40 as illustrated in FIG. 2. The container holder shown is of a rectangular shape with a top surface 42 having six apertures 44 extending therethrough. Of course, alternatives can include container holders defined by other shapes and less or greater than six apertures. The apertures are sized to fit the cross sectional area of tubes 10 and include screw threads 46 on an interior surface defining a circumference of each aperture. Screw thread 46 allows screw thread 14 of body 10 of a retrieved tube to be secured to container holder 40. The container holder is an aluminum plate. Alternatively, other materials known to those of ordinary skill in the art can be used.

In one embodiment, the tray is injection molded with apertures sized to fit Axygen brand O-ring caps used in conjunction with Axygen ST-150 tubes. The tray is further sized to fit three six-tube sets of tubes at 18 mm spacing.

In another embodiment, the caps of the tubes include anti-rotation knurling on an outer circumferential surface 17 (FIG. 1 illustrates location of outer circumferential surface as shown in an embodiment described above). An inner surface of the tubular extensions surrounding each aperture in the tray also include anti-rotation knurling, so that that cap resists rotation when the rotary tool is rotated to remove the body from the cap.

In another embodiment, the tray can include extensions surrounding each aperture with perimeters that are polygonal or otherwise non-circular in shape in place of the tubular extensions. The dimensions of the extension in such embodiments is sufficient to support any forces from the cap inside the extension as the body of the tube is rotated for removal. In other embodiments, the flange on the outside perimeter of the tray is at an acute or oblique angle or has a non-linear cross section along its length. In other embodiments, the tray and the caps can be monolithic. In others, the tray can also include a handle member for carrying the tray. In further embodiments, the tray can include an available surface for identification of contents in the tubes stored in the apertures of the tray.

In other embodiments, the rotary tool can have a non-cylindrical shape and/or a non-cylindrical cavity to accommodate a shape of the container used. In another embodiment, the interior surface of the rotary tool can include engagement features other than splines such as other protrusions as referenced above or recesses. Similarly, protrusions other than splines or other engagement features can be included on the surface of the body of each tube.

Figure 3:
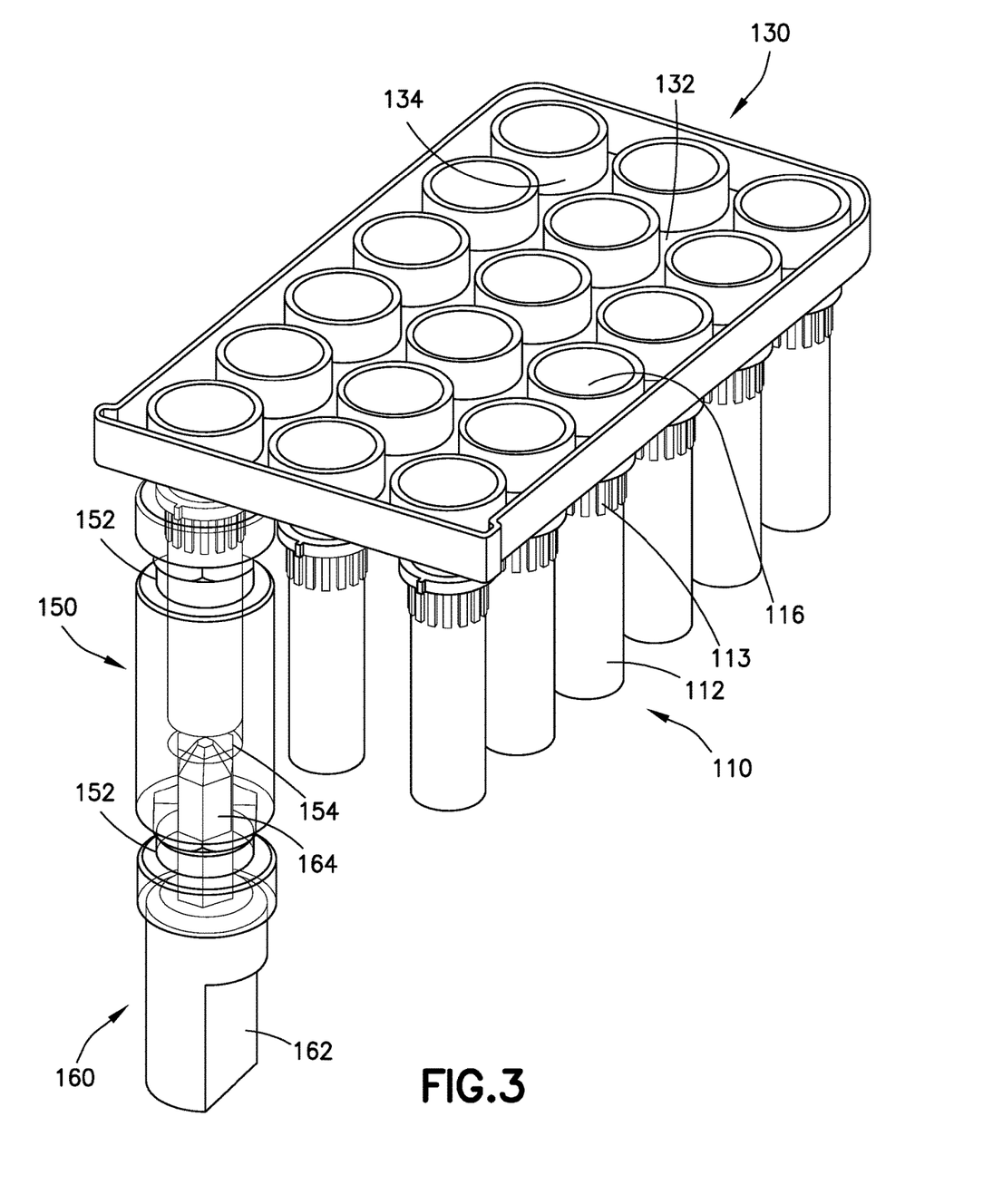
FIG. 3 illustrates a second embodiment including a tray holding a plurality of tubes and a socket member with rotary tool inserted over one of the tubes. The socket member is illustrated in phantom.
Figure 4:
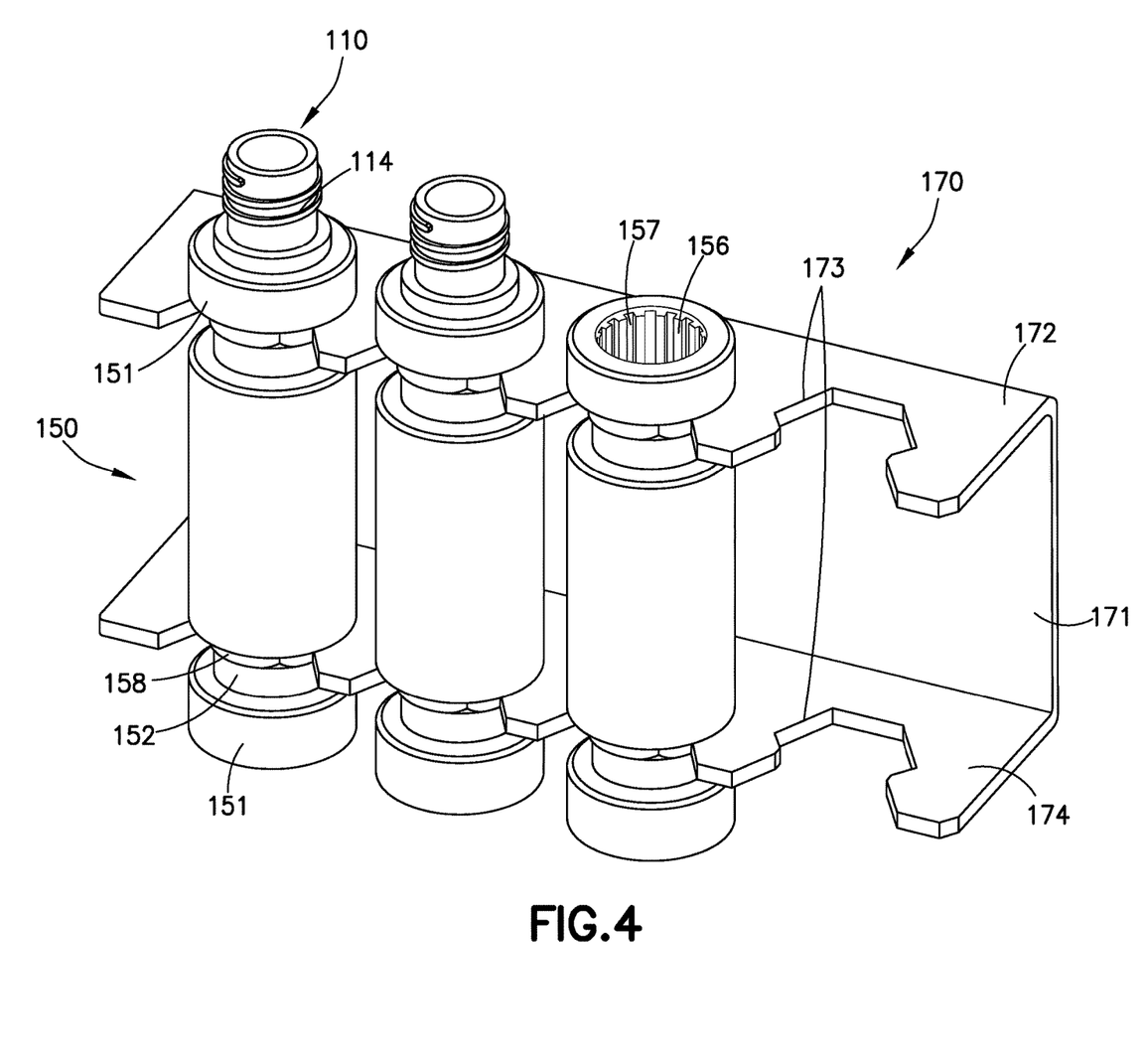
FIG. 4 illustrates three of the individual socket members illustrated in FIG. 3 placed in a socket holder. Two of the socket members shown include a decapped tube disposed therein while the third socket member is empty.

In another embodiment of the first aspect, the system includes a socket member 150, a socket rotary tool 160 and a tray 130. The socket member as shown in FIG. 3 has a substantially cylindrical shape. The diameter of the socket member is the same at each end 151 and in a central portion, but also includes two recessed cylindrical portions 152 separating the end portions from the central portion. Within the recessed portions are anti-rotation features 158, visible in FIG. 4. The socket member also includes openings extending from each longitudinal end. At one end is an opening with a hexagonal cross-sectional shape 154 extending into the socket member 150 in a longitudinal direction over a first length and defining a first cavity, as shown in FIG. 3. In a variant, the cross section of the opening over the first length can be any polygonal shape. From another end is a circular cross-sectional shaped opening 156 extending into the socket member in a longitudinal direction over a second length and defining a second cavity. On an interior surface of the circular section opening, defining the outer bounds of the cavity circumference, are longitudinal splines 157 as shown in FIG. 4. The first cavity corresponds with socket rotary tool 160, described in greater detail below, and the second cavity corresponds with tube 110. Further, longitudinal splines 157 correspond with splines 113 (FIGS. 3 and 4). In the depicted embodiment, hexagonal opening 154 and circular opening 156 do not overlap or make contact. However, it is contemplated that the cavities can abut one another to define a single passage through the socket member. The socket member is made of stainless steel. In a variant, the material of the socket member can be any known to those of skill in the art.

Socket rotary tool 160 includes a handle portion 162 and an engagement portion 164. As shown in FIG. 3, the engagement portion is a structural member with a hexagonal section sized to fit into the first cavity through hexagonal opening 154. This type of engagement portion is sometimes referred to as a hex drive shaft. At one end, the engagement portion includes a tapered tip. Handle portion 162 is substantially cylindrical in shape but includes a flat portion towards an outer end for gripping purposes. At an inner end of the handle portion is a flat surface beveled at the edges from which engagement portion 164 extends. Of course, contours of the handle portion and interface with the engagement portion can be modified based on knowledge of one of ordinary skill in the art.

As in FIG. 1, FIG. 3 also shows tray 130 holding a plurality of tubes in suspension. The tray and structure for holding tubes is the same as described in the embodiment above. Circular opening 156 of socket member 150 is shaped to slide and otherwise fit over a body 112 of each tube 110 as in the above embodiments.

In a variant, the system shown in FIG. 3 can also include a socket holder 170, as shown in FIG. 4. The socket holder is a storage instrument that can hold socket members 150. This can be for various purposes, including pipetting. Because each tube body can be held within a socket member, the storage of socket members also allows for the storage of decapped tubes, as shown. Socket holder 170 includes an upper flange 172 and a lower flange 174, both extending from a central portion 171. Each flange includes an outer edge with recessed or otherwise jagged portions 173 along its length. Recesses 173 are shaped to accommodate recessed cylindrical portions 152 of the socket member. A neck in recessed edge 173, combined with anti-rotation features 158, allows socket members to be secured to the socket holder when pressed into flanges 172, 174. When stored in the socket holder, each end portion 151 of the socket member rests entirely outside flanges 172, 174. When in place in the socket holder, the socket member is restrained from any rotational movement and any movement along its longitudinal axis. The socket holder is made of a stainless steel sheet. Alternatively, it can be made of any material known to those of skill in the art.

In another embodiment, each of the first cavity and the second cavity can have any cross-sectional shape and together can define any combination of cross-sectional shapes. For example, the first cavity can have an octagonal cross-section and the second cavity can have an elliptical cross section. As with the rotary tool and tubes described above, it is contemplated that the socket member can include any type of engagement feature on its interior surface. Similarly, the engagement portion of the socket rotary tool can be any shape corresponding to the first cavity of the socket member.

In any one of the above embodiments, the tray and the container holder or socket holder can be housed within an instrument. In some embodiments, the tray can be housed within an instrument while the container holder or socket holder are not, and vice versa.

In any one of the above embodiments, the rotary tool or socket member can be connected to an automated device to mechanically control the movement of the rotary tool or socket member. For example, a three axis robotic arm attached to the rotary tool can be controlled to transport the rotary tool below a tube, slide it over a body of the tube and then cause the tool to rotate to remove the body from a cap of the tube.

In other embodiments, the socket member and/or socket rotary tool can have a non-cylindrical shape. The socket member can further include a non-cylindrical cavity extending from a non-circular opening over the second length to accommodate a shape of the container used.

Advantages of the system include that fewer elements are needed to access a reagent or sample from storage than with known systems. For example, no motor is needed in the embodiments described herein and there is no cap-grabbing mechanism needed. Moreover, the space required for the tray, rotary tool or socket member and containers is minimal, particularly compared with known systems. The system is also simple. A container body can be retrieved with a cap removed through one removal step using a rotary tool. No additional mechanisms or elements are required to address cap removal specifically.

With regard to the socket member embodiment specifically, one advantage is that the circular opening in the socket member is located high above a surface of the top flange of the socket holder when held in place by the socket holder. This reduces the risk of contamination.

In another aspect, the invention relates to a method of decapping containers by removing the body of a container from a tray holding a capped container in suspension. The body of the container is then placed in another location for pipetting or another use. The entire process is performed using tools as described herein.

In one embodiment, one or more capped tubes are obtained. The tubes are pressed into open apertures on top surface 32 of tray 30, body 12 side first, until a top surface of cap 16 is flush with a top surface of tubular extension 34 and locked in place with an anti-rotation feature as described above. In this position, the inserted tube is suspended from the tray, as shown in FIG. 1. Rotary tool 20 is then obtained and longitudinally aligned with a tube that a user intends to decap ("desired tube"). The rotary tool is then slid over the desired tube until splines 13 of the desired tube are no longer visible.

With rotary tool 20 in place over the desired tube (e.g., 10 in FIG. 1), the user rotates the rotary tool in a counterclockwise direction until body 12 of tube 10 is removed from cap 16. All that is needed to hold the body of tube 12 upright is rotary tool 20 itself. The rotary tool holding the body of the tube is then transferred to another location as desired.

In a variant, the user can transfer tool 20 holding the tube to container holder 40 for storage or pipetting. The user positions rotary tool 20 directly below an aperture 44 in the container holder and moves the tool upward until a top surface of the body of the tube contacts edges of the aperture in the container holder. The user then rotates the tool in a clockwise direction and screw threads 14 of the tube interact with screw threads 46 on the surface of the insertion aperture. The tool is rotated until the body of the tube is secured to container holder 40 and at least a portion of the body is exposed above container holder surface 42, as shown in FIG. 2. Once secured, a user can access the contents of each tube as desired. For example, pipetting can be done with the tubes secured to the container holder.

In another embodiment, socket member 150 and socket rotary tool 160 are used to retrieve body 12 of tube 10. First, the tubes are pressed through apertures 134 in a surface 132 of the tray and suspended therefrom as described above. Then, socket rotary tool 160 is engaged to socket member 150 by inserting the hexagonal drive shaft of engagement portion 164 into hexagonal opening 154 of the socket. The combined socket member and tool are then slid over body 112 of the tube sought to be decapped and retrieved. As in the above embodiment, socket member 150 is slid over body 112 until splines 113 on the surface of the tube match splines 156 within the circular opening of the socket member. Socket rotary tool 160 is then rotated counterclockwise until body 112 of the tube is removed from cap 116.

As in the previous embodiment, the tube can be transported as desired. In a variant, socket member 150 holding the tube can be placed into socket holder 170 for pipetting or temporary storage as shown in FIG. 3. Recesses 173 on the outer edge of the flanges of the socket holder provide means for the socket member to be clipped in. This is achieved by placing recessed portions 152 of the socket member into recesses 173 on the edge of the flanges. In particular, anti-rotation features 58 on recessed portions 152 of the socket member, when clipped into flange recesses 173, form an interlocking connection with recesses 173. This connection ensures that the socket member does not rotate and that it does not move relative to a longitudinal axis of the socket member. To achieve this connection, the user presses the socket in, and lowers the socket to obtain engagement with the anti-rotation features. To leave the socket in place, the user continues to lower the socket rotary tool until it disengages from the socket member.

In any one of the above embodiments, the automated device can be used to control the movement of either the rotary tool or the socket member. In particular, the automated device can control the rotary tool or the socket member to remove the body of the tube from the tray and then transfer it to another location. The automated device can also perform the same steps in reverse and place the body of the tube back into the cap in the tray.

In any one of the above embodiments, the tubes placed into the tray can be filled with a reagent or sample prior to placement. In still further embodiments, any given tray can store tubes that hold different reagents or samples. In a variant, when more than one reagent or sample type is stored on a tray, tubes holding common reagents or samples can be retrieved together so that each type of reagent or sample can be analyzed separately and the risk of contamination is reduced.

In any one of the above embodiments, color coding can be used for the tubes to aid in identifying types and quantities of reagents or samples taken from the tray.

In other embodiments, if the reagents or samples in the plurality of tubes can cause contamination if mixed or spilled, then each tube may be transferred to a location other than a container holder for pipetting so that each individual tube can be analyzed separately. Alternatively, a socket member can retrieve a tube body as described above and transfer the retrieved tube body to a socket holder via the socket member, thus minimizing the risk of contamination.

In any one of the above embodiments, the tubes filled with reagents or samples can be kept in cold temperature storage. Generally, cold temperature storage improves shelf life of reagents or samples disposed within the tubes.

The above methods can be performed with any embodiment of the systems contemplated herein.

Advantages of the method described include that fewer steps are required to retrieve an opened body of a container from a tray to transport it to another location for pipetting or another use. For example, one step that is no longer required is the removal of a cap prior to removal of the body of the container. This advantage of not having to perform this step is magnified by the fact that known methods also required a recapping step to place the container into storage after use. With the methods herein, both of these steps are no longer necessary.

Other advantages include that the risk of error is lower with the methods described herein because fewer steps are required than those previously understood to be necessary. For similar reasons, the risk of contamination is also reduced. In some embodiments, the use of cold temperature storage increases the volume of reagent or sample that can be stored in one container, thus lowering cost.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system to access and retrieve screw-top containers, the system comprising:

a tray including a plurality of apertures extending therethrough, at least one of the apertures having a container therein, each container having a cap and body such that each cap of each container placed into the tray rests above a respective aperture in the tray and each body is suspended below the tray;

a rotary tool comprising a cavity extending from an opening at one end of the rotary tool, the cavity defined by an interior surface wherein the interior surface comprises engagement features, the rotary tool further comprising a socket member having a length between a first end and a second end, a first cavity in the socket member having a first cross-section extending longitudinally from the first end toward the second end and a second cavity in the socket member having a second cross-section extending longitudinally from the second end toward the first end, an inner surface defining a circumference of the second cavity wherein the engagement features are located on the inner surface proximate the second end, wherein the first and second cavity abut one another to define a single passage through the socket member or are separated from one another; and the rotary tool further comprising a handle portion and an engagement portion, the engagement portion having a cross-sectional shape adapted to fit within the first cavity in the socket member;

wherein the engagement features on the interior surface of the socket member and on a surface of the body of the container are longitudinally oriented splines.

2. The system of claim 1, wherein the socket member is cylindrical in shape and includes two recessed portions along its length, each recessed portion including anti-rotation features.

3. The system of claim 2 further comprising a socket holder, the socket holder including an upper and lower flange extending from a central portion in a transverse direction, each flange including an edge with recesses adapted to secure the recessed portions of the socket member within.

4. The system of claim 1, wherein the tray and the cap of each container are monolithic.

5. The system of claim 1, wherein a shape of a surface of the tray proximal to each aperture is adapted to guide the body of the container into the cap above the surface of the tray.

6. The system of claim 1, wherein an outer circumferential surface of the cap of each container includes knurling that provides resistance to rotation when positioned in the tray, wherein the tray has tubular extensions sized to interact with the cap of each container surrounding the respective aperture, and wherein an interior surface of each tubular extension includes knurling.

* * * * *